United States Patent [19]

Meek et al.

[11] Plant 4,921

[45] Nov. 2, 1982

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 184,404

[22] Filed: Sep. 4, 1980

[51] Int. Cl.[3] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named El Charo having flat capitulum form; daisy capitulum type; orange-bronze ray floret color with rapid color oxidation; yellow-green (immature) to yellow (mature) disc floret color; diameter across face of capitulum ranging from 70 to 90 mm. at maturity; uniform nine week photoperiodic flowering response to short days; tall plant height when grown as a single stem cut spray; medium peduncle length; and minimum pollen production.

2 Drawing Figures

The present invention comprises a new and distinct cultivar of *Chrysanthemum morifolium,* Ramat., hereinafter referred to by the cultivar name El Charo.

El Charo is an induced mutation of Charisma, disclosed in U.S. Plant Pat. No. 4,561. El Charo was discovered and selected as one flowering plant within a flowering block of the parental seedling by William E. Duffett on Jan. 18, 1979 in a controlled environment in Salinas, Calif. Plants within the flowering block were derived from stock plants which had been irradiated as unrooted cuttings with an x-ray source of 2600 R units.

The first act of asexual reproduction of El Charo was accomplished when vegetative cuttings were taken from the initial selection in April, 1979 in a controlled environment in Salinas, Calif. by a technician working under formulations established and supervised by Jack M. Meek. Continued asexual reproduction by vegetative cuttings for evaluative tests in flowering and stock programs in conjunction with horticultural examination of selected plants initiated July 31, 1979 has demonstrated that the combination of characteristics as herein disclosed for El Charo are firmly fixed and are retained through successive generations of asexual reproduction.

El Charo has not been observed under all possible environmental conditions. The phenotype may vary significantly with variations in environment such as temperature, light intensity and day length. The following observations, measurements and comparisons describe plants grown in Salinas, Calif. under greenhouse conditions which approximate those generally used in commercial practice.

The following traits have been repeatedly observed and are determined to be basic characteristics of El Charo which in combination distinguish this chrysanthemum as a new and distinct cultivar:

(1) flat capitulum form, (2) daisy capitulum type, (3) orange-bronze ray floret color with rapid color oxidation, (4) yellow-green (immature) to yellow (mature) disc floret color, (5) diameter across face of capitulum ranging from 70 to 90 mm. at maturity, (6) uniform nine week photoperiodic flowering response to short days, (7) tall plant height (attaining a height as a flowered plant of 70 to 75 cm. from a rooted cutting planted to short days for April through November flowerings), (8) medium peduncle length, and (9) minimal pollen production.

Of the many commercial cultivars known to the present inventors, the most similar in comparison to El Charo are Charisma and Bronze Marble, an unpatented cultivar. Reference is made to attached Chart A which compares certain characteristics of El Charo to those same characteristics of Charisma and Bronze Marble.

In comparison to Charisma, El Charo has different ray floret color. The capitulum form, capitulum type, diameter across face of capitulum, plant height, flowering response period and peduncle length of Charisma are similar to those same characteristics of El Charo.

In comparison to Bronze Marble, El Charo has different ray floret color, larger diameter across face of capitulum, taller plant height and shorter peduncle length. The capitulum form, capitulum type and flowering response period of Bronze Marble are similar to those same characteristics of El Charo.

The accompanying drawings show typical inflorescence characteristics of El Charo. Sheet 1 comprises a photographic drawing of a cut spray of El Charo and accurately shows the ray and disc floret color values. Sheet 2 is an enlarged black and white photograph showing in greater detail the inflorescence of a cut spray of El Charo.

In the following description, color references are made to The Royal Horticultural Color Chart. The color values were determined between 1:30 and 2:00 P.M. on July 17, 1980 under 100 foot-candle light intensity at Salinas, Calif.

Classification:

*Botanical.*—*Chrysanthemum morifolium,* Ramat., cv El Charo.

*Commercial.*—Cut daisy spray.

I. INFLORESCENCE

A. Capitulum:

*Form.*—Flat.

*Type.*—Daisy.

*Diameter across face.*—70 to 90 mm.

B. Corolla of ray florets:

*General tonality from a distance of* 3 *meters.*—180-B over 170-C.

*Color* (*abaxial*).—Approximately 178-C over 35-B (immature) oxidizing rapidly to 180-B streaked lightly over 190-C (immature).

*Color* (*adaxial*).—Approximately 178-C streaked over 35-B (immature) to 180-B streaked lightly over 190-C.

C. Corolla of disc florets:

*Color.*—Ranging from 154-A to 13-A (immature) to 13-A to 17-B (mature).

D. Reproductive organs:

*Androecium.*—Present disc florets only; scant to few; scant pollen.

*Gynoecium.*—Present both ray and disc florets.

II. PLANT

A. General appearance:

*Height.*—Tall, 70 to 75 cm.

*Branching pattern.*—Semi-upright.

B. Foliage:

*Color* (*abaxial*).—Approximately 137-A.

*Color* (*adaxial*).—137-C overlaid with white.

*Shape.*—Deeply lobed and coarsely serrated.

CHART A

COMPARISON OF EL CHARO, CHARISMA AND BRONZE MARBLE

| CULTIVAR | RAY FLORET COLOR | CAPITULUM FORM & TYPE | DIAMETER ACROSS FACE OF CAPITULUM |
|---|---|---|---|
| EL CHARO | Orange-bronze with rapid color oxidation | Flat Daisy | 70 to 90 mm. |
| CHARISMA | Dark lavender pink with rapid oxidation | Flat Daisy | 70 to 90 mm. |
| BRONZE MARBLE | Medium bronze with rapid oxidation | Flat Daisy | 60 to 85 mm. |

CHART A-continued

COMPARISON OF EL CHARO, CHARISMA AND BRONZE MARBLE

| CULTIVAR | PLANT HEIGHT | FLOWERING RESPONSE PERIOD | PEDUNCLE LENGTH |
|---|---|---|---|
| EL CHARO | Tall 70 to 75 cm. | 9 week | Medium from 80 to 110 mm. |
| CHARISMA | Tall 70 to 75 cm. | 9 week | Medium, from 85 to 110 mm. |
| BRONZE MARBLE | Medium 60 to 70 cm. | 9 week | Long, 150 to 200 mm. |

COMPARISONS MADE OF PLANTS GROWN AS SINGLE STEM CUT SPRAYS WITH NO LONG DAYS IN SALINAS, CALIFORNIA

We claim:

1. A new and distinct cultivar *Chrysanthemum morifolium,* Ramat., plant known by the cultivar name El Charo, as described and illustrated, and particularly characterized as to uniqueness by the combined characteristics of flat capitulum form; daisy capitulum type; orange-bronze ray floret color with rapid color oxidation; yellow green (immature) to yellow (mature) disc floret color; diameter across face of capitulum ranging from 70 to 90 mm. at maturity; uniform nine week photoperiodic flowering response to short days; tall plant height, medium peduncle length; and minimum pollen production.

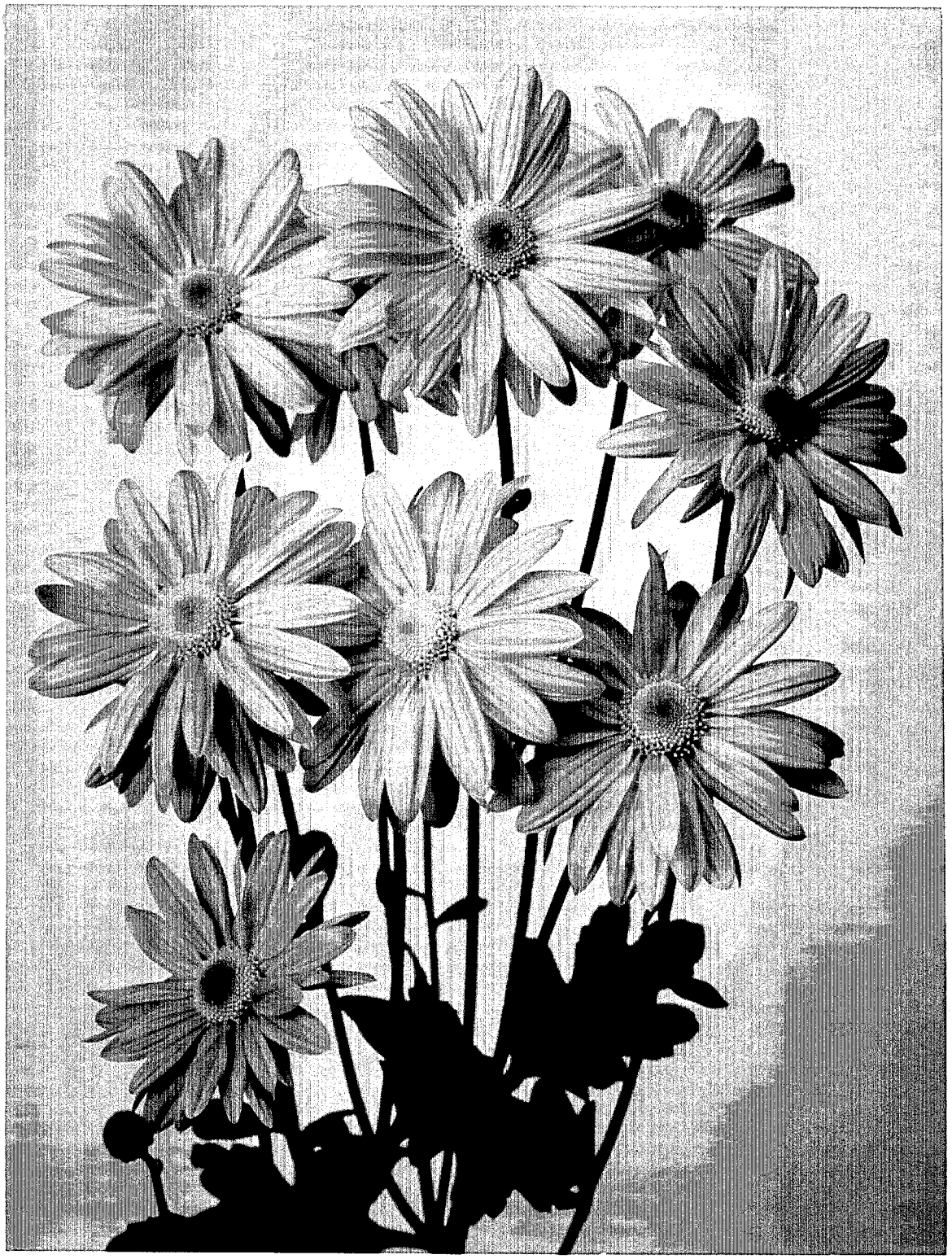

* * * * *